United States Patent [19]
Garman et al.

[11] Patent Number: 6,022,686
[45] Date of Patent: Feb. 8, 2000

[54] ASSAY METHOD

[75] Inventors: Andrew John Garman, Ashton; Robert Stanley Moore, Comerbach, both of United Kingdom

[73] Assignee: Zeneca Limited, London, United Kingdom

[21] Appl. No.: 08/101,105

[22] Filed: Aug. 3, 1993

Related U.S. Application Data

[63] Continuation of application No. 07/935,338, Aug. 27, 1992, abandoned, which is a continuation of application No. 07/476,605, Feb. 7, 1990, abandoned.

[30] Foreign Application Priority Data

Feb. 7, 1989 [GB] United Kingdom .................. 8902689

[51] Int. Cl.[7] .............................. C12Q 1/68; G01N 33/48
[52] U.S. Cl. ................................ 435/6; 435/5; 435/91.1; 436/501; 436/94
[58] Field of Search ...................... 435/5, 6, 91; 436/501, 436/94

[56] References Cited

U.S. PATENT DOCUMENTS

| | | | |
|---|---|---|---|
| 4,257,774 | 3/1981 | Richardson et al. ...................... | 23/230 |
| 4,476,228 | 10/1984 | Huchgermeier et al. ............... | 436/500 |
| 4,668,640 | 5/1987 | Wang et al. ........................... | 436/536 |
| 4,670,380 | 6/1987 | Dattegupta ................................. | 435/6 |
| 4,683,194 | 7/1987 | Saiki et al. ................................. | 435/6 |
| 4,766,062 | 8/1988 | Diamond et al. ......................... | 435/6 |
| 4,820,630 | 4/1989 | Taub ........................................ | 435/6 |
| 4,863,876 | 9/1989 | Hevey ..................................... | 436/537 |
| 4,959,463 | 9/1990 | Froehler et al. ......................... | 536/27 |
| 5,185,439 | 2/1993 | Arnold, Jr. et al. .................... | 536/24.3 |

FOREIGN PATENT DOCUMENTS

| | | | |
|---|---|---|---|
| 0201184 | 3/1986 | European Pat. Off. . | |
| 0232967 | 8/1987 | European Pat. Off. .................. | 435/6 |
| 0312248 | 10/1988 | European Pat. Off. . | |
| 0232967 | 1/1989 | European Pat. Off. . | |
| 0297379 | 1/1989 | European Pat. Off. .................. | 435/6 |
| 0320308 | 6/1989 | European Pat. Off. . | |
| 90 75958 | 3/1990 | Japan . | |
| WO8805538 | 7/1988 | WIPO . | |

OTHER PUBLICATIONS

Bloomfield et al. Physical Chemistry of Nucleic Acids Harper & Row NYNY (1974) pp. 456–460.
Morrison et al., "Solution–Phase Detection of Polynucleotides . . . ", *Analytical Biochem.*, 183, 231–244(1989).
Urdea et al., "A comparison of non–radioisotopic hybridization . . . ", *NAR*, 16(11) 1988.
Asseline et al., "Oligodeoxynucleotide, covelently linked . . . ", *EMBO*, 3(4), 795–800, 1984.
Syranen et al., "Quantification of polymerase chain Reaction . . . ", *NAR*, 16(23) 1988.
Kobayashi, Tamiya and Karube (1988) a translation of the Preprint No. 1 IXC 18 entitled "New Assay Method for DNA Using Fluorescence Depolarization", contained in Collection 1 of Preprints of Lectures at the 56th Annual Spring Convention of Nihon Kagaku–Kai.
Matthews et al, "Review, Analytical Strategies for the Use of DNA Probes", Analytical Biochemistry, vol. 169, No. 1, Feb. 15, 1988, p. 1–25.
Gyllenstein et al, "Generation of Single–Stranded DNA by the Polymerase Chain Reaction and its Application to Direct Sequencing of the HLA–DQA Locus", Proc. Natl Acad. Sci. USA vol. 85, pp. 762–7656, Oct. 1988, Genetics.
Chemical Abstracts 105:204923z "Association of short DNA fragments: steady state fluorescence polarization study"; Hard et al & Bio–polymers 1986, vol. 25, No. 8, pp. 1519–1529.
Brumbaugh et al, "Continuous, on–line DNA Sequencing Using Oligodeoxynucleotide Primers with Multiple Fluorophores", Proc. Natl Acad Sci USA, vol. 85, pp. 5610–5614, Aug. 1988, Genetics.
Arnold, Jr. et al, "Assay Formats Involving Acridinium–Ester–Labeled DNA Probes," Clin. Chem. 3578, 1588–1594 (1989), vol. 35, No. 8, 1989.
Database WPIL/dERWENT, abstract No. 86–343471 (52), 1986, Derwent Publications Ltd., London, GB; & JP–A–61258168 (Ind. Res. Inst. of Japan) 15.ll.1986.
Morrisen et al, Solhon–Phase Delzehan/polynucleotides. Analytical Biochem. 183, 231–244 (1989).
Urdea, et al, A comparison of non– . . . isotopic/Bridgeham NAR, 16 (11) 1988.
Asseline et al otzoch . . . pro . . . EMBO, 34) 795–800, 1984.
Syvanen et al, Nucleic Acids Res., v. 16, 1988, 11327–38.
S. Kobayashi et al., New Assay Method for DNA Using Fluorescence Depolarization, Proc. Chemical Sensors, 1987, p. 370.
W.B. Dandliker et al., "Fluorescence Polarization Immunoassay, Theory and Experiment Method", Immunochemistry, 1973, vol. 10, pp. 219–227.
Brumbaugh et al, "Continuous, on–line DNA Sequencing Using Oligodeoxynucleotide Primers with Multiple Fluorophores", Proc. Natl Acad Sci USA, vol. 85, pp. 5610–5614, Aug. 1988, Genetics.
Arnold, Jr. et al, "Assay Formats Involving Acridinium–Ester–Labeled DNA Probes," Clin. Chem. 3578, 1588–1594 (1989), vol. 35, No. 8, 1989.
Database WPIL/dERWENT, abstract No. 86–343471 (52), 1986, Derwent Publications Ltd., London, GB; & JP—A—61258168 (Ind. Res. Inst. of Japan) 15.11.1986.

*Primary Examiner*—George C. Elliott
*Assistant Examiner*—Sean McGarry
*Attorney, Agent, or Firm*—Pillsbury Madison & Sutro, LLP Intellectual Property Group

[57] ABSTRACT

Assay method for the detection of nucleic acid sequences in homogeneous solution. The method comprises the use of fluorescence polarisation to detect hybridisation of a fluorescent nucleic acid probe or to detect fluorescent primer extension products. Assay kits for use in the above methods.

21 Claims, 3 Drawing Sheets

Fig. 1.

ASSAY METHOD

This is a continuation of application Ser. No. 07/935,338, filed on Aug. 27, 1992, now abandoned, which was abandoned upon the filling hereof which was a FWC of 07/476,605, filed Feb. 7, 1990, now abandoned.

The present invention relates to a novel method for the detection of nucleic acid sequences, and in particular to the use of fluorescently labelled nucleic acid probes.

Methods presently available for detecting nucleic acid sequences involve a relatively large number of steps and are laborious to perform. Some of the well-established methods are described for example in Hybridisation, by B. D. Hames and S. J. Higgins (Eds) IRL Press 1985 and J. A. Matthews et al, Analytical Biochemistry, 169, 1988, 1–25 (Academic Press). Typically the DNA to be assayed is denatured and bound to a solid support, eg. nitrocellulose or nylon, and then incubated with a probe sequence, complementary to the target, which contains a label, for example $^{32}P$, or one half of an affinity pair, for example biotin. After incubation and washing of the solid phase, it is then developed to give a signal, by autoradiography for $^{32}P$, or in the case of biotin, typically by the addition of an avidin-enzyme conjugate, further washing and then substrate. Also sandwich assays are known, whereby a capture nucleic acid probe, of sequence complementary to the target, is bound to a convenient solid support. This is then allowed to hybridise to the target sequence. A labelled probe is then allowed to hybridise to another part of the target sequence, and after washing steps, the label is developed as appropriate. Alternatively, the "sandwich" is formed in solution with two probes, one containing the label and the other containing one half of an affinity pair. After hybridisation, the solution is then contacted with the solid phase to which the other half of the affinity pair is bound, Washing and signal development then takes place. All these methods and their variants require numerous handling steps, incubations, washings, and the like which result in processes which are both laborious and time-consuming.

K. Kleppe et al in J. Mol. Biol. (1971), 56, 341–361 disclose a method for the amplification of a desired DNA sequence. The method involves denaturation of a DNA duplex to form single strands. The denaturation step is carried out in the presence of a sufficiently large excess of two nucleic acid primers which upon cooling hybridise to regions adjacent to the desired DNA sequence. Two structures are thus obtained each containing the full length of the template strand appropriately complexed with primer. DNA polymerase and a sufficient amount of each required deoxynucleoside triphosphate are added whereby two molecules of the original duplex are obtained. The above cycle of denaturation, primer annealing, and extension are repeated until the appropriate number of copies of the desired DNA sequence is obtained. It is indicated that adjustment of the primer concentration may be required. The above method is now referred to as the polymerase chain reaction (PCR), as described for example in European Patent Application, Publication No. 0 201 184. Methods for detecting amplified nucleic acid sequences, for example DNA sequences generated by PCR, are as outlined above. Alternatively, they can be analysed by gel electrophoresis, and the existence of a band of a given molecular weight is taken as evidence of the presence of the sequence in the original DNA sample, as defined by the specific primers used in the amplification reaction. Again such methods are relatively time-consuming and laborious.

It is therefore desirable to provide a method for the detection of nucleic acid sequences which ameliorates at least in part the above mentioned problems. The present invention is based on the discovery that hybridisation of a fluorescent nucleic acid probe to a target nucleic acid sequence, or extension of a fluorescent nucleic acid primer into an elongated chain may be detected by fluorescence polarisation and that useful diagnostic assays may be devised using this principle.

Fluorescent labels have been used in a range of assays for biological molecules. A particularly useful form of fluorescence assay is that involving the use of fluorescence polarisation as described by Dandliker and Feigen, Biochem. Biophys. Res. Comm. 5, 299–304 (1961). In this immunoassay, there is provided a fluorescently tagged analyte molecule which competes with the analyte molecule for the specific antibody. The extent of binding to the antibody is determined by measurement of the fluorescence polarisation, a quantity that for a given fluorophore under given conditions depends on the volume or to an approximation, the molecular weight of the species to which the fluorophore is attached. Thus the method is able to discriminate between antibody-bound and free fluorophore. In brief the fluorescence polarisation of a sample is measured by stimulating the sample with polarised light and measuring the polarisation of the emitted light. Large, slowly tumbling molecules will move less between the absorption and the emission of the photon and hence the emitted light will show a high degree of polarisation. Conversely, smaller molecules will show a lower degree of polarisation (see Principles of Fluorescence Spectroscopy, J. E. Lakowicz, 1983, Plenum). A principal advantage of this type of immunoassay is that it is homogeneous ie. does not involve separation steps. However, the fluorescence polarisation immunoassay technique has been restricted to low molecular weight analytes, that is analytes having a molecular weight of less than about 1,000 such as drugs and low molecular weight hormones such as thyroxine. Analogous assays for nucleic acid sequences cannot be readily devised since antibodies recognising single or double stranded nucleic acids with useful sequence specificity are not known.

The method of the present invention is applicable to molecular biology research and to all areas of diagnostic medicine and other diagnostic sciences, for example forensic, agricultural, veterinary or food sciences where it is necessary to detect or measure specific nucleic acid sequences. In particular it is applicable to the detection of infectious micro-organisms and to the detection of point mutations, gene deletions and rearrangements which give rise to various inherited diseases and predispositions. A further application of the method of the present invention is that it may be used to measure nucleic acids that are themselves generated as part of an assay signal system, for example the RNA sequence that is generated by Qβ replicase as described in Nucleic Acids Research, 14, 5591–5603, (1986) or Biotechnology, Vol 6, pages 1197–1202, (October 1988). A particularly advantageous use for the method of this invention is for the assay of DNA sequences which have been generated by polymerase chain reaction (PCR) as hereinbefore described. Further advantageous uses of the method of the present invention are in relation to the transcription based nucleic acid amplification/detection systems of Siska Diagnostics Inc. described in PCT patent publication WO 88/10315 and the ligase mediated amplification system of Biotechnica International (EP-320308).

A particular advantage of the method of the present invention is that it may be carried out in a homogeneous phase, for example in the solution phase. This means that in general, only a single addition of a reagent containing one or more polynucleotide species, such as polynucleotide probes, to the sample DNA is required with the consequent saving in time and labour. In general, only a single incubation is involved and separation, washing and electrophoretic steps are avoided.

According to a first aspect of the present invention there is provided a method for the detection of a target nucleic acid sequence in a sample which method comprises contacting the sample nucleic acid with a fluorescent nucleotide probe capable of hybridisation with the target nucleic acid sequence in homogeneous solution and detecting the presence or absence of such hybridisation by fluorescence polarisation.

The sample is generally of biological origin, for example obtained from humans, plants and/or animals. The target nucleic acid is generally prokaryotic and/or eukaryotic nucleic acid or an amplification product thereof. Convenient aspects of the present invention include the detection of human or animal DNA sequences such as human DNA sequences.

The polynucleotide probes used in the method of the invention include polynucleotides of DNA, RNA or any other kind hybridisable to nucleic acid sequences. It will be appreciated that such nucleic acid sequences may include base analogues as well as the naturally occuring bases cytosine, adenine, guanine, thymine and uracil. Such base analogues include hypoxanthine, 2,6-diaminopurine and 8-azaguanine. The probes may be in double stranded (ds) or single stranded (ss) form but are preferably in single stranded form. They may be prepared by direct synthesis, polymerase mediated extension reactions or by cloning or any other convenient method. These nucleotide probes are fluorescently labelled as hereinafter described.

The expression "hybridisation" as used herein includes hybridisation between a polynucleotide probe and a desired target sequence but excludes hybridisation between a polynucleotide probe and non-desired nucleotide sequences. Suitable conditions for hybridisation are well known to the scientist of ordinary skill, see for example "Nucleic Acid Hybridisation", B. D. Hames and S. J. Higgins (Eds), IRL Press, Oxford, 1985. In general the fluorescent probe is added to the target nucleic acid such that a substantial degree of hybridisation takes place in a convenient time period prior to measurement. Convenient temperatures for hybridisation include ambient temperature, typically 20 to 25° C., as well as other temperatures below the melting temperature of the probe and the target nucleic acid. The pH of the reaction buffer is generally neutral or moderately alkaline, for example pH 7.5 to 9.0 and the ionic strength is chosen such that the desired hybridisation occurs but unwanted hybridisation with other sequences is excluded. The effect of the variables mentioned above is well known in the literature, for example in "Nucleic Acid Hybridisation", B. D. Hames and S. J. Higgins (Eds), IRL Press, Oxford, 1985.

The distinguishing power of the probe is generally maximised by 100 per cent homology with the target nucleotide sequence but this is not essential and any convenient degreee of homology may be chosen such as at least 70%, at least 80%, or at least 90%, preferably at least 95% homology, provided that only the desired hybridisation can occur under the hybridisation conditions employed. The length of the polynucleotide probe will depend on the specificity requirements of the chosen hybridisation and is also selected according to the molecular weight of the target nucleic acid. In general for the detection of, for example, human genomic DNA sequences using the above method of the present invention a polynucleotide probe of at least 17 bases is required to achieve an acceptable level of specificity. (Wallace et al, Proc. Natl. Acad. Sci. 80, 278, 1983). The upper limit of the length of the polynucleotide probe is determined by the convenience of synthesis and is generally about 100 bases. Normally the length will be in the range 10–40 bases. However sequences which have been amplified, for example, by the PCR reaction, can also be detected using shorter polynucleotide probes without impairing selectivity. For example, a human gene sequence that is amplified by, for example, a million-fold, may be detected using polynucleotide probes of 6–20 bases long, for example 8–15 bases without compromising selectivity. Normally the above conditions can be met by polynucleotides of less than 30 bases long, more preferably less than 20 bases long. The length of the polynucleotide probe is conveniently chosen such that a measurable increase in molecular weight takes place upon binding to the target sequence. Generally at least a two-fold increase in molecular weight is selected, but for maximum sensitivity and reliability, a greater increase is desirable.

It is to be understood that fluorescence polarisation includes all analytical methods which comprise analysis of polarisation of light emitted from the fluorophore comprised in the polynucleotide probe when excited by polarised light. In particular this includes the analysis of the emitted light from the fluorophore when excited by plane polarised light. This is outlined, for example in a paper by M. E. Jolley (J. Analytical Toxicology, 5, pages 236–240, (1981)).

Homogeneous solutions include any solution having solutes in the liquid phase. This also includes suspensions with fine suspensions or colloids or related mixtures which are sufficiently transparent or non-scattering to enable fluorescence polarisation measurements to be made.

The concentration of the fluorescent probe is conveniently selected to be lower or approximately equal to the lowest expected concentration of the target, that is to say the probe is not provided in a large excess over the target. This is desirable since any unhybridised fluorescent probe would continue to give a low polarisation and it would be more difficult to detect the higher polarisation of the hybrid, particularly since the polarisation of species in mixtures are not additive and the observed polarisation is more strongly influenced by the species of lowest polarisation. In assays where the range of target sample nucleic acid concentration cannot be readily predicted it will be appreciated that the concentration of the fluorescent probe used will effectively determine the sensitivity of the assay. Where the target nucleic acid sequence is generated by an amplification step, for example polymerase chain reaction (PCR), the amplification is conveniently carried out so that the amount of amplified nucleic acid generated is generally constant and a suitable concentration of fluorescent probe can then be readily chosen, either by calculation or by appropriate routine experimentation.

As stated above a particularly advantageous use for the method of the invention is for the assay of DNA sequences which have been generated by polymerase chain reaction (PCR). Therefore in a further aspect of the present invention the target nucleic acid sequence is a product of sample nucleic acid amplification, for example sample DNA amplification.

A common feature of nucleic acid hybridisation is that after denaturation to separate the sample nucleic acid strands the sample nucleic acid strand complementary to the sample nucleic acid sequence of interest competes with the fluorescent probe for hybridisation with the sequence of interest. If the fluorescent probe is displaced by the complementary strand, hybridisation may not occur, or occur only at an unacceptable degree of sensitivity. In respect of polymerase chain reaction (PCR) this problem may be eliminated or at least alleviated by the application of the following aspects:

It has been found that relatively short PCR products, conveniently those of less than 100 base pairs in length, may be used as polynucleotides containing a target nucleotide sequence. In such instances, the strand complementary to that chosen to be the target strand, is not significantly larger than the probe sequence and competition is thereby reduced. For example a PCR product of 80 base pairs, generated by two 30 mer primers spaced 20 base pairs apart, may be detected by a 16-mer, complementary to one of the sequences in the intervening 20 base pair section.

It has been found that certain versions of nucleic acid amplification processes which are able to generate essen- tially single stranded products, such as the asymmetric polymerase chain reaction (PCR) for example as described by Gyllensten U. B. et al, P.N.A.S., 1988, 85, 7652, or PCR followed by exonuclease treatment for example as described by Higuchi R. G. et al, Nucl. Acids. Res., 1989, 17, 5865, are well suited to the above methods and alleviate the displacement problem referred to above.

The preferred asymmetric method involves performing the PCR reaction with a first primer in excess over a second primer which is present at a lower than usual concentration, typically 10–100 nM. Thus it is possible to generate one polynucleotide strand in excess over the complementary strand by employing in the amplification reactions unequal concentrations of the two primers. For example, a standard 100 μl PCR reaction employing 100 pmoles of a first primer and 2 pmoles of a second primer in combination with a target nucleotide sequence will produce an excess of the strand generated by the first primer, which can be detected using a fluorescent probe for example using the direct probe approach of the present invention.

In a further aspect of the method of the present invention blocking nucleic acids may be conveniently added to prevent strand displacement, either before or at the same time as the polynucleotide probe is added. The blocking nucleotide sequences bind to regions adjacent to, on one or both sides of, the target sequence recognised by the probe. These blocking nucleic acids, being conveniently synthetic oligonucleotides of 10–100 bases long, preferably 20–50 bases long, may be conveniently employed at higher concentrations than the probe itself and may thereby compete with the complementary strand and allow the polynucleotide probe to bind to the target. The above situation is conveniently illustrated thus:

A further aspect of the present invention involves the use of more than one polynucleotide probe to mutually block each other and to thus inhibit binding of the complementary strand. This format may bring about an improvement in sensitivity by increasing the precision of the fluoresence polarisation measurement. This embodiment is conveniently illustrated thus:

The precise number of blocking nucleic acids and polynucleotide probes used will depend on a number of factors such as the length of the target strand, its base composition etc. and the optimum number may be readily determined by the scientist of ordinary skill for example by appropriate experimentation.

The above aspects of the present invention are conveniently referred to hereinafter as the direct probe approach.

In a further aspect of the present invention we provide a method for the detection of a target nucleic acid sequence in a sample, which method comprises contacting the sample with (i) a complementary polynucleotide capable of hybridisation to the target nucleotide sequence and (ii) a fluorescent polynucleotide probe capable of hybridisation to the same region on the complementary polynucleotide, in homogeneous solution and detecting by fluorescence polarisation the presence or absence of hybridisation of the fluorescent polynucleotide probe with the complementary polynucleotide.

In this aspect the target nucleic acid sequence and the fluorescent probe compete for the same region on the complementary polynucleotide. This aspect is therefore a competitive hybridisation assay. As previously explained the nucleotide sequences and hybridisation conditions are selected so as to exclude hybridisation with non-desired nucleotide sequences.

In general the complementary polynucleotide will comprise a double stranded or single stranded nucleic acid species such as DNA or RNA, preferably a single stranded nucleic acid species, for example single stranded DNA. The complementary polynucleotide is preferably a synthetic oligonucleotide. Convenient lengths for the complementary polynucleotide include at least 15 bases and preferably at least 30 bases.

The concentrations of the reagents are so arranged that in the absence in the sample of the target nucleic acid of interest the fluorescent probe is bound to the complementary polynucleotide, whilst in the presence of the target nucleic acid sequence the fluorescent probe is displaced or remains unbound. Since, in the latter case the fluorophore is attached to a lower molecular weight species, a lower fluorescence polarisation value is observed. The assay may be designed such that the affinity between the fluorescent probe and the complementary polynucleotide is lower than that between the target nucleic acid sequence of interest and the complementary polynucleotide. This affinity may be adjusted by judicious selection of the length of the fluorescent probe and the complementary polynucleotide. Alternatively, the affinity between the fluorescent probe and the complementary polynucleotide may be lowered by the incorporation of one or a small number of mismatches or the use of non-naturally ocurring base analogues. Selection of convenient length and sequence for the fluorescent probe and the complementary polynucleotide may be readily determined by the scientist of ordinary skill. Preferably the length of the complementary polynucleotide will be longer than the fluorescent probe to give a greater change in the molecular weight of the species attached to the fluorophore and hence a more detectable change in polarisation. The upper limit for the length of the complementary polynucleotide is in general determined by convenience, for example in the case of synthetic oligonucleotides it is preferably less than 100 bases.

The order and timing of reagent addition in the above competitive hybridisation assay may be determined by the scientist of ordinary skill. In general the fluorescent probe is first contacted with the sample and subsequently with the complementary polynucleotide.

The target nucleic acid sequences to be assayed according to the preceeding aspects of the invention are according to any of the convenient or preferred aspects set out hereinbefore in respect of the direct probe approach.

The above aspects of the invention are conveniently referred to hereinafter as the competitive hybridisation assay approach.

It will be noted that, in the case of double stranded nucleic acid targets after denaturation the fluorescent probe may bind to one of the sample DNA strands resulting in a high polarisation value and thus falsely suggesting the absence of the sample nucleic acid sequence of interest. A preferred aspect of the methods of the present invention is therefore the detection of substantially single-stranded nucleic acid, such as may be readily generated by the various amplification procedures and their variants as described above.

The present invention also relates to the incorporation of a fluorescent nucleic acid primer into an elongated chain followed by detecting the presence or absence of the elongated chain by fluorescence polarisation.

According to a further aspect of the invention there is provided a method for the detection of a target nucleic acid sequence in a sample which comprises contacting sample nucleic acid with a fluorescent polynucleotide primer capable of hybridisation with the target sequence, subjecting any hybrid formed to primer extension and detecting the presence or absence of primer extended product by fluorescence polarisation.

Primer extension is generally effected enzymatically and may for example be followed by strand separation, annealing of further polynucleotide primer and enzymatic extension thereof. The above procedure may be repeated as many times as desired. A procedure which comprises the above steps and replicates both strands using two primers is, for example the method disclosed by K. Kleppe et al in J. Mol. Biol. (1971), 56, 341–361 for the amplification of a desired DNA sequence and referred to in European Patent Application, Publication No. 0 201 184 as the polymerase chain reaction. The detection of the presence or absence of incorporation of the primer using fluorescence polarisation can be achieved at any stage of the procedure outlined above, most conveniently after completion of the above procedure. It will be appreciated that the fluorescent nucleic acid primer is selected so that recognition by the polymerase enzyme employed is not impaired to any extent. The above method may for example be performed with two fluorescent primers or more conveniently with one fluorescent primer and one non-fluorescent primer.

Convenient conditions for the performance of polymerase chain reaction include the use of for example 1$\mu$g or less of sample DNA which is conveniently mixed with typically 50–150 $\mu$L of buffer of for example pH 7.2–8.8 containing typically 1 mM concentrations of dATP, dCTP, dGTP and dTTP. Specific primer oligonucleotides are added (1 nM–2 $\mu$M). These primers are typically 15 to 40 nucleotides long and their sequences correspond to the 5' ends of both strands. The above mixture is thoroughly denatured by heating, typically to 90–100, for example 100 degrees C. for 1–10 minutes. Upon cooling to below 50 degrees C., typically 0.5–5 units of a heat stable polymerase for example the DNA polymerase from Thermus aquaticus, are added. The amplification is achieved by a series of thermal cycles which typically include a denaturation step at 85–95 degrees C. for ½ to 3 minutes, an optional annealing step at 40–65 degrees C. also for ½ to 3 minutes and a polymerase extension step at 60–80 degrees C. for a time which has been optimised for the sequence in question and which is typically from 5 seconds to 3 minutes. These steps are repeated between 15 and 50, such as between 15 and 40, times in a typical reaction.

It is known that in conventional PCR reactions, the amplification reaction comes to completion before all the primers are consumed. In the above mentioned PCR aspects of the invention it would therefore be necessary to detect the higher molecular weight fluorescent extension product in the presence of low molecular weight fluorescent primers which would normally be in a significant excess. This would place great demands on the sensitivity and precision of the fluorescence polarisation measurement. One solution would be to separate out by chromatography or electrophoresis the fluorescent PCR product, but this is time-consuming and not preferred. The preferred method is to perform the PCR reaction with a first non-fluorescent primer in excess over a second fluorescent primer which is present at a lower than usual concentration, typically 10–100 nM. Thus all or most of the fluorescent primer becomes extended and hence gives rise to an increased polarisation value. For example, a standard 100 $\mu$l PCR reaction employing 100 pmoles of a first primer and 2 pmoles of a second fluorescent primer will ensure substantially complete incorporation of the fluorescent primer.

Advantageously the detection methods of the present invention are performed in conjunction with the Amplification Refractory Mutation System (ARMS) described by C. R. Newton et al in Nucleic Acids Research, 1989, 17, 7, 2503–2516 and claimed in European patent application, publication no. 332435 (ICI). In brief the method comprises (i) contacting a nucleic acid sample with a diagnostic primer which is substantially complementary to a diagnostic portion of a target base sequence, whereby extension of the diagnostic portion on a target template under appropriate conditions is only achieved when a terminal nucleotide of the diagnostic primer is complementary to either a suspected variant nucleotide or a corresponding normal nucleotide of the target base sequence, and (ii) detecting the presence or absence of an extension product. ARMS may therefore be performed using either fluorescent probe(s) to detect the presence or absence of amplification products according to the direct probe approach of the invention or by using appropriate fluorescent primer(s) and detecting the presence or absence of primer extension or by the competitive hybridisation approach as hereinbefore described.

All the diagnostic methods of the present invention may also be used for the detection of a number of different nucleic acid sequences of interest in a single test. This is provided by the use of different fluorophores, each fluorophore being indicative of the presence of a specific sequence. The number of sequences detectable in a single assay is only limited essentially to the number of suitable fluorophores, for example having different spectral properties, specifically of different excitation and/or emission wavelengths, that can be identified and comprised in the polynucleotide probes.

The different nucleic acid sequences of interest are for example alleles of a genetic locus. This is of particular importance in the detection of genetic disorders, caused by for example point mutations, translocations or deletions and will in general allow the detection in sample DNA from an individual of normal and mutant alleles in a single test.

Therefore according to a further aspect of the present invention the target nucleic acid sequences correspond to alleles of a genetic locus indicative of an inherited disease, disorder or predisposition.

Detection of the presence or absence of the target nucleic acid sequences is conveniently effected for example using the Amplification Refractory Mutation System hereinbefore described. Alternatively hybridisation with allele specific fluorescent nucleic acid probes according to the direct probe approach of the invention is employed, conveniently after polymerase chain reaction amplification of the sample nucleic acid.

Since it is commonly of interest to determine whether a patient is homozygous or heterozygous for a particular allele of a genetic locus, two such determinations using different allele specific probes would typically be required. For example, in the diagnosis of cystic fibrosis using the major mutation, the Phe 508 deletion (Kerem et al., Science 1989, 245, 1073) the test would involve a determination using a probe which hybridises to the normal sequence and also a determination with a probe which hybridises to the mutant sequence. The three possible outcomes would therefore give results:

|  | N/N | N/M | M/M |
| --- | --- | --- | --- |
| normal probe | + | + | − |
| mutant probe | − | + | + |

(where N and M represent normal and mutant alleles and "+" indicates an increased polarisation value).

The above described diagnostic test might involve two separate assays. In a preferred aspect of the invention the test for two or more target nucleic acid sequences is performed in a single reaction vessel. This is achieved by labelling each allele specific nucleic acid probe with a different fluorophore, contacting the probes with the target nucleic acid and determining the polarisation of fluorescence for each fluorophore, for example using an instrument capable of making the necessary changes in excitation wavelength and the wavelength at which the light is measured. Optionally, where the nucleic acid is the product of an amplification reaction, a probe to check that the amplification reaction had proceeded may be employed. However in the CF diagnosis example given above, the table shows that a general failure of any amplification reaction would manifest itself uniquely as a low polarisation with both probes.

The methods of the present invention are conveniently used to detect the presence or absence of one or more target bacterial or viral nucleic acid sequences in a sample. A further convenient aspect of the the claimed method is the detection in a single vessel of nucleic acid sequences, such as DNA sequences from two or more different strains of bacteria or viruses.

In all the preceding aspects of the present invention there is a change in molecular weight of the species attached to the fluorophore which is detected by fluorescence polarisation. It is desirable for this change to be as large as possible in order to make the detection methods sensitive, robust and to minimise interference.

Advantageously the hybridised nucleic acid to be detected by fluorescence polarisation is attached to a macromolecule so as to increase the change in molecular weight to be detected. The actual means used to attach the macromolecule will depend on the particular aspect employed and may occur either prior or subsequent to probe-target hybridisation.

Any convenient macromolecule can be used provided that it does not adversely affect the performance of the method of the invention. Proteins are convenient macromolecules and for example high molecular weight proteins, for example bovine serum albumin, thyroglobulin or keyhole limpet hemocyanin, or alternatively a water soluble polymer such as dextran or a polyamino acid may be employed. The molecular weight of the macromolecule conjugate is preferably selected so as to significantly increase the molecular weight of the probe conjugate, convenient ranges of weight include more than 3,000 daltons, such as more than 8000 daltons, more than 15000 daltons, more than 30000 daltons, most preferably more than 100,000 daltons. The upper limit for the molecular weight of the macromolecule is generally limited by physical parameters such as viscosity and solubility. It is believed that insoluble polymeric species such as nanobeads or sub-micron latices may be suitable, provided that they do not cause an unacceptable degree of scattering of light in the sample.

The type of attachment will depend on the particular aspect employed:

For the direct probe approach, the sample nucleic acid is contacted both with one or more fluorescent probes as hereinbefore described as well as one or more macromolecularised polynucleotide(s). A macromolecularised polynucleotide includes conjugates of single stranded nucleic acid, conveniently an oligonucleotide, with a macromolecule as outlined above.

Therefore according to a further aspect of the method of the invention the hybridised species to be detected by fluorescence polarisation includes one or more macromolecule-polynucleotide conjugates hybridised to the target nucleic acid sequence.

The following diagram illustrates one possible arrangement of fluorescent probes and macromolecularised polynucleotides:

where M indicates a macromolecularised polynucleotide and F indicates a fluorescent probe.

The optimum arrangement of these species may be determined by the scientist of ordinary skill for example by routine experimentation.

In the competitive assay approach the complementary single stranded target nucleic acid sequence is conjugated to a macromolecule for example as hereinbefore outlined in respect of the direct probe approach. The resulting conjugate is used in the competitive assay as hereinbefore described. This results in a higher polarisation of the mixture in the absence of the sample nucleic sequence of interest.

Therefore in a further aspect of the competitive assay approach one or more macromolecules are attached to the complementary polynucleotide.

Incorporation of the macromolecule can be either via non-covalent or covalent bonding. Procedures for the covalent attachment of macromolecules such as proteins to oligonucleotides are known, for example as disclosed by European Patent 202758. The preferred chemistry for the attachment of non-proteinaceous macromolecules will depend on the particular macromolecule and what functional groups are available for linkage. Macromolecules which comprise primary amino functions, or groups that can readily be derivatised to give amino functions, can be treated as proteins and procedures based on those referred to above can be employed. Those containing carboxyl functions or which can be derivatised to give carboxyls can be coupled using carbodi-imide or active ester chemistry to amino-derivatised oligonucleotides. For covalent attachment the polynucleotide is conveniently a synthetic oligonucleotide.

Non-covalent attachment is conveniently effected via specific binding substances, one substance is attached to the polynucleotide and the other is attached to the macromolecule. Examples of convenient specific binding substances include biotin and streptavidin or avidin, hapten and anti-hapten antibody, or oligosaccharide and specific lectin. Biotin and streptavidin or avidin are particularly preferred specific binding substances. In order to maximise the desired increase in the polarisation change, it is preferable to attach the lower molecular weight partner to the polynucleotide and the higher molecular weight partner to the macromolecule. For some assays that the higher molecular weight partner of the pair may itself be of sufficient molecular weight to achieve the desired increase in the change in polarisation and consequently conjugation to a further macromolecule is unnecessary. Non-covalent linkage is conveniently employed where the polynucleotide is prepared by a polymerase-mediated primer extension reaction. Here a binding pair partner may be introduced by use of a modified nucleoside triphosphate. Non-covalent linkage between specific binding substances can be effected at any convenient time during the method of the present invention. The addition of the second binding substance to the assay vessel is before hybridisation, after hybridisation or at the same time as the polynucleotide component.

In the fluorescent primer approach the polymerase chain reaction is carried out wherein one of the primers is fluorescently labelled as described above and the second primer is linked to a macromolecule for example as described above provided that the macromolecule is attached to the primer in such a way that the extension reaction is not significantly inhibited and that the macromolecule is stable that is to say it does not denature and precipitate at the temperatures and other conditions employed in the amplification reaction. It is therefore preferred that the macromolecule is not attached to the 3' end of the primer and proteins which are liable to denature and precipitate in the amplification reaction are not employed. To ensure a high percentage incorporation of the fluorescent primer, this is preferably present at reduced concentrations as hereinbefore described, for example the other primer is present in 10–100 fold excess. It is however not generally necessary to reduce the concentration of macromolecularised primer used in the polymerase chain reaction amplification.

In respect of non-covalent attachment of macromolecules it is preferable to add the macromolecule conjugate after the amplification reaction. For example, the PCR amplification reaction could be designed as described above but with a biotinylated primer, for example a 5' biotinylated primer, as the second (non-fluorescent) primer. In an asymmetric PCR amplification this primer is present at the higher concentration. After the PCR reaction the macromolecule conjugate may then be added before the polarisation measurement. Methods for biotinylating oligonucleotides are known, for example as described in European Patent 202758 (ICI) or by the use of reagents such as amino-derivatised oligonucleotides described in the catalogue of Calbiochem Corporation.

Alternatively, one binding substance, preferably the lower molecular weight component, for example biotin, may be incorporated in the amplification reaction such as versions of PCR as described above which give rise to single stranded products. This may be achieved by the use of one or more biotinylated primers, for example 5'-biotinylated primers, or by the incorporation of biotinylated nucleotides such as biotin-[$\gamma$]-aminobutyryl-[$\epsilon$]-amidocaproyl-[5-(amidoallyl)-2' deoxy-uridine-5'-triphosphate] (Langer P. R. et al., Proc. Natl. Acad. Sci. (1981), 78, 6633), supplied in the amplification buffer at a concentration, which may be selected by routine experiment, to give optimum incorporation of biotin.

After amplification, the presence of target DNA may then be detected by the direct probe approach of the invention having first incubated the amplified target with the macromolecule conjugate, in this example a macromolecule avidin or streptavidin conjugate. This approach may employ other binding pairs, for example, it may employ primers or deoxynucleoside triphosphates derivatised with a hapten, and enhancement of polarisation using an antibody macromolecule conjugate.

Sample DNA which may or may not contain the target nucleic acid sequence for use in the method of the present invention may be pre-treated using standard methods known in the art. These treatments may involve steps such as heating, treatment with strongly alkaline solutions, proteinase K, detergents as appropriate. In general it is desirable that the DNA is rendered single stranded prior to adding the probe, for example by heating, but this will depend on the type of assay. Optionally it may be appropriate to cleave the sample DNA using one or more restriction enzymes.

Conveniently the probes and primers used according to the invention are synthetic oligonucleotides. Such oligonucleotides can be readily synthesised by methods known in the art (see, for example, Oligonucleotide Synthesis by M J Gait, IRL Press) and a number of chemistries are known for attaching labels, in this case, fluorophores to these oligonucleotides. There are two principal types of linkage. The first involves attachment at either the 5' or the 3' end of the oligonucleotide using a suitable linker group. Suitable linkers are aminoalkyl groups, in particular aminohexyl, which can be readily attached to the 5' end during oligonucleotide synthesis, see for example Agrawal S. et al, Nucl Acids Res, 14, (1986), 6227- and WO-88/02004 (Applied Biosystems). The amino group is then reacted with activated fluorophore derivatives such as fluorescein isothiocyanate. Alternatively the fluorophore may be attached to the base moieties. For example the exocyclic amino group of the base cytosine is a convenient attachment point; alternatively a wide variety of other linkages to other atoms on the base moieties are possible, see for example Ruth et al, DNA, 1985, 4, 93 and Letsinger, J. Am Chem Soc, 1981, 103, 7394. Derivatives of cytosine containing aminoalkyl groups attached to the ring amino group can be incorporated using oligonucleotide synthesis and subsequently reacted with activated fluorophores. A further approach is to employ base analogues which are themselves fluorescent for example as is described in H Inoue et al, Nucleic Acids Research, 13, 7119 (1985). Although it is convenient to attach one fluorophore per probe it may be advantageous in some circumstances, where increased sensitivity is required, to attach more than one fluorophore per probe. The essential feature of all the attachment methods is that the ability to hybridise with the target nucleic acid sequence should not be significantly impaired, nor in the fluorescent primer extension approach should the priming ability of the primer be impaired. In this latter case, 3' attachment of the fluorophore is generally inappropriate.

Alternatively the fluorescent probes and primers employed in the method of the invention and in particular the fluorescent probes, may be made by a polymerase mediated extension reaction using as a template a section of nucleic acid known to have the desired hybridisation for the target nucleic acid, or its complementary strand. The fluorophore may be introduced either by the use of a primer which has been labelled with a fluorophore, conveniently at the 5' terminus, or by the incorporation of fluorescent nucleotide analogues or of nucleotides to which a fluorophore has been attached, for example on the exocyclic amino group of cytosine or the 5 position of uridine and attached such that the desired hybridisation is not subsequently compromised.

A fluorophore for use in the method of the invention may be conveniently selected using the following guidelines:

a. It has sufficiently high quantum yield and molar absorptivity to provide the desired sensitivity for the assay b. It has relatively low molecular weight, preferably less than 5000, more preferably less than 1000.

c. It has a fluorescence lifetime comparable to the rotation times of the molecules employed in the assay. This aspect is discussed more fully in M E Jolley, J. Analyt, Toxicol. 5, 236–240, (1981).

d. In respect of polymerase chain reaction it must be heat stable.

e. It should preferably not be a strong intercalator since this will cause the probe to bind non-specifically to non-target DNA in the sample and give erroneously high polarisation readings.

The above guidelines comprise a wide range of fluorophores, such as fluorescein, rhodamine, tetramethyl rhodamine, sulphorhodamine 101, pyrene and dansyl, conveniently fluorescein and rhodamine, such as fluorescein.

Such fluorophores may be conveniently conjugated for example to an amino group of a polynucleotide by the use of for example isothiocyanate derivatives, succinimidyl esters or sulphony halide derivatives or conjugated to thiol derivatised polynucleotides using for example maleimido derivatives. Other reactive derivatives of fluorophores are also known, as shown for example in the catalogue of Molecular Probes, Inc.

An assay may involve a single polarisation determination taken after the hybridisations of the assay are complete. Alternatively, in order to eliminate possible artefacts, it is preferable to also determine the polarisation of the fluorescent probe or primer prior to the assay and thus measure a change in polarisation. This may be measured in a polarising fluorimeter, typically a fluorimeter with polarising elements such as filters, prisms or liquid crystals positioned in the emission light path and the excitation light path, for example according to methods described by Jolley, J. Analyt, Toxicol. 5, 236–2490 (1981). Essentially this comprises measuring the horizontally and vertically polarised light emitted when the sample is irradiated with either horizontally (H) or vertically (V) polarised light. The polarisation value, for a sample irradiated with vertical light, is given by $$P = \frac{(I_{11})_v - (I_\perp)_v}{(I_{11})_v + (I_\perp)_v}$$

where 11 indicates polarisers parallel and $\underline{1}$ indicates polarisers perpendicular. This may be corrected to allow for instrument bias by using $$P = \frac{(I_{11})_v - G(I_\perp)_v}{(I_{11})_v + G(I_\perp)_v}$$

-continued $$\text{where } G = \frac{(I_{11})H}{(I_\perp)H}$$

where 11 indicates emission polariser parallel to the vertical and 1 indicates emission polariser perpendicular to the vertical.

In practice, in controlled assays, the change in polarisation may be such that only two, or even one, reading is required, excluding replicates, to indicate the presence of the nucleic acid sequence.

The determination can be carried out in a wide variety of fluorimeters equipped with polarising elements. Such fluorimeters may be either in the "L" format, where the emitted light is measured at 90° to the excitation beam, or the "T" format where it is measured both at 90 and 270°. This latter orientation allows for fixed polarising elements such that the vertical and horizontal components can be analysed simultaneously. In order to improve sensitivity, laser light sources, for example an Argon ion laser, may be used. In order to allow measurement of different fluorophores, provision may be made for changing the excitation and/or emission wavelengths, whether by use of gratings, filters or switching light sources.

It will be appreciated that scattered light is highly polarised and at low fluorescent polynucleotide concentrations care should be exercised to ensure that this is not a significant interference. In such cases, the effect of scattered light can be minimised by use of sample pre-treatment procedures to remove dust, particulates and the light, and by the use of appropriate experimental controls.

It will be appreciated that the assays of the present invention may be made quantitative by reference to a standard curve which may be constructed using solutions of target nucleic acid of known concentration.

The polarising fluorimeter may form part of a dedicated assay instrument with automated or semi-automated liquid and/or cartridge handling facilities. The assay kit of the invention includes reagents and/or cartridges that can be run on automated or semi-automated assay instrumentation. Such instrumentation may provide for the initial amplification of the sample nucleic acid such as sample DNA, by for example the PCR technique, and accordingly may contain a controlled heating block and/or automated liquid transfer.

The present invention also comprises an assay kit for use in any aspect of the invention as defined above. The assay kit comprises (depending on the particular embodiment employed) a solution of the probe(s) or probe primer(s), and/or complementary polynucleotides as defined above and conveniently buffered, and optionally together with other solutions for the pre-treatment of the DNA, as described above, and buffer solutions to allow the hybridisation reaction to take place with the required kinetics, affinity and specificity. Such conditions will depend on the assay temperature and may be conveniently determined by experimentation. The kit also comprises suitable instructions for carrying out the claimed method.

The invention will now be illustrated but not limited by reference to the following Examples and figures wherein:

MATERIALS AND METHODS

Abbreviations

The following abbreviations apply:

| | |
|---|---|
| SMCC | succinimidyl 4-(N-maleimidomethyl)cyclohexane-1-carboxylate |
| Tris | tris(hydroxymethyl)aminomethane |
| BSA | bovine serum albumin |
| PBS | 0.13 M NaCl, 5.4 mM $Na_2HPO_4$, 1.6 mM $KH_2PO_4$ buffer pH 7.3 |
| SSC | 20x SSC is 3 M NaCl, 0.3 M trisodium citrate |
| DMF | dimethyl formamide |
| FITC | fluorescein isothiocyanate |

1. Oligonucleotide Synthesis

The following oligodeoxyribonucleotides were synthesised on a DNA synthesiser (Applied Biosystems 380B) using protocols recommended by the manufacturer. After deprotection in concentrated ammonia the oligonucleotides were evaporated to dryness on a concentrator (Savant Speedvac) and re-dissolved in 1.0 ml of water.

Oligonucleotide 1

LGCGTTTAG-3' bases 7552–7559 of the human $\alpha_1$ anti-trypsin gene

Oligonucleotide 2

5'-CTAAACGCCTAAACGCCTAAACGCCTAAACGCCTAAACGCCTAAACGCCTAAACGC-3' a synthetic 64 mer containing 8 repeats of complement to oligo nucleotide 1

Oligonucleotide 3

5'-ATTCGCTTAAGATTTTGGCTGATTCCATTAACAGTAAGTAATTTACACCTTACGAGGCCACTCG an unrelated 65 mer Oligonucleotide 4

5'-TGCCACCGCCATCTTCTTCCTGCCTGATGA-3' PCR primer: bases 7627–7656 of the human $\alpha_1$ antitrypsin gene Oligonucleotide 5

5'-TGGTGATGATATCGTGGGTGAGTTCATTTT-3' PCR primer: bases complementary to 7677–7706 of the human $\alpha_1$ antitrypsin gene Oligonucleotide 6

LGGAAACTACAGCACCT-3' bases 7659–7674 of the human $\alpha_1$ antitrypsin gene

Oligonucleotide 7

5'-CCCACCTTCCCCTCTCTCCAGGCAAATGGG-3' PCR primer: bases 7440–7469 of the human $\alpha_1$ antitrypsin gene Oligonucleotide 8

5'-GGGCCTCAGTCCCAACATGGCTAAGAGGTG-3' PCR primer: bases complementary to 7770–7799 of the human $\alpha_1$ antitrypsin gene Oligonucleotide 9

5'-GGAATCACCTTCTGTCTTCATTTTCCAGGAACTTGG
TGATGATATCGTGGGTGAGTTCATTTTCCAGGTGCTGTAGTTTCCCCTCATCAGGCAGGAA-3'
97-mer target oligonucleotide, bases complentary to 7643–7739 of the human $\alpha_1$ antitrypsin -gene Oligonucleotide 10

5'-GGCGGGAAGGGCGACTGCCGCCAAAATGCCGACGATGGCGAT
CACAATCATCAGCTCGATAAGGGTAAAGCCTTTTTGAAGGGTATTCAT-3' 90-mer target oligonucleotide, complentary to bases 725–824 of the Pilin E gene of *Neisseria gonorrhoeae*

Oligonucleotide 11 LTCGAGCTGATGATTGT-3' bases 767–782 of the Pilin E gene of *Neisseria gonorrhoeae*

Oligonucleotide 12 LTTCCTGCCTGATGAG-3' bases 7643–7657 of the $\alpha_1$-antitrypsin gene

```
Oligonucleotide 13   LGAAAATGAACTCACC-3'  bases 7676-7690 of the
α₁-antitrypsin gene

Oligonucleotide 14   LACGATATCATCACCA-3'  bases 7692-7706 of the
α₁-antitrypsin gene Oligonucleotide 15   LGGTGAGTTCATTTTC-3'  complementary to
oligonucleotide 13
```

In the above table, the bases in the human alpha-1 anti-trypsin gene are as used by Long G. L. et al, Biochemistry, 1984, 23, 4828–4837. The letters A G C and T refer to the bases adenine, guanine, cytosine and thymine, respectively, whilst the letter L refers to the amino-linker group:

which is derived from the following reagent by reaction with a 5' terminal hydroxyl group on the automated synthesiser, using the essentially the same protocol as for addition of the nucleotide elements. The protecting trifluoroacetyl group is removed during the recommended concentrated ammonia deprotection step.

2. Fluoresceinylation of the 5' (aminohexylphosphoryl) Oligonucleotides (FL-oligos)

Method A:

Ca. 30 nmole of the 5' (aminohexylphosphoryl) oligonucleotide was diluted to 0.2 ml with water and desalted on a NAP-10 Sephadex G-25M gel filtration column (Pharmacia) equilibrated in 0.5% triethylamine to give 0.7 ml of desalted product. To this was added a 4 mg/ml solution fluorescein isothiocyanate (isomer 1, Sigma, 0.3 ml) in methanol, and the reaction allowed to proceed for one hour in a water bath at 55° C. The solution was then neutralised by the addition of 20 μl of 1M tris(hydroxymethyl) aminomethane pH 7.5 and applied to a Sephadex G25M PD-10 column (Pharmacia) equilibrated with 10 mM tris (hydroxymethyl)aminomethane 1 mM EDTA, pH 8.0. The desalted product, 1.6 ml, was then concentrated on a concentrator (Savant Speedvac) to a volume of ca. 0.4 ml. Purification was achieved by reverse phase hplc on a Waters C18 micro Bondapak column using LKB hplc equipment with the absorbance detector set at 495 nm. The column was equilibrated with eluent A, 0.1M triethylammonium acetate pH 7.0 at a flow rate of 1.0 ml/min and, after sample application, a 0 to 60% linear gradient of eluent B, 100% acetonitrile, was applied over 60 minutes. Fractions showing absorbance at 495 nm, due to fluorescein, were pooled and analysed by spectroscopy. From the optical density at 260 nm and 495 nm a fluorescein content of ca. 0.7 to 0.8 mole/mole DNA was calculated.

Method B:

To the amino derivatised oligonucleotide in water (120 ul) was added 1M sodium carbonate/bicarbonate buffer pH 9.0 (60 ul), followed by a 1% solution of FITC in dry DMF (20 ul). Reaction was allowed to proceed at ambient temperature (25° C.) in the dark for 3 hours, after which it was de-salted on a NAP-5 gel filtration column (Pharmacia) equilibrated in PBS, taking the excluded fraction (0.8 ml) This was subsequently purified on hplc essentially as described above but with buffer B as 80% acetonitrile/water and a 45 minute gradient.

3. Polymerase Chain Reaction

The reactions were performed in autoclaved 0.5 ml microcentrifuge tubes (Alpha Laboratories) containing the following:

0.025 to 1 μg human genomic DNA
10 μl 100 mM Tris HCl, 500 mM KCl, 15 mM MgCl₂, 0.1% gelatin (w/v) pH 8.3
6 μl d NTPs (3.33 mM dATP, 3.33 mM dCTP, 3.33 mM dGTP, 3.33 mM dTTP)
100 pmoles 3' primer
2 or more pmoles 5' primer
Water to 100 μl (Millipore Reagent Grade Water System)

These tubes were boiled for 5 minutes to denature the genomic DNA and then allowed to cool to room temperature. 2 units of Thermus aquaticus DNA polymerase (New England Biolabs or Cetus) were added to each tube which was then overlayed with 50 μl of Light Mineral Oil (Sigma).

DNA amplification was performed using the polymerase chain reaction on a Techne intelligent heating block or a Perkin-Elmer Cetus DNA thermal cycler using the following conditions (unless otherwise stated):

| | | |
|---|---|---|
| Segment 1 | Temperature 91° C. | Time 2 minutes |
| Segment 2 | Temperature 60° C. | Time 3 minutes |
| Segment 3 | Temperature 72° C. | Time 2 minutes |
| Cycles = 36 | | |

Amplifications referred to in examples 6 to 9 employed:

| | | |
|---|---|---|
| Segment 1 | Temperature 94° C. | Time 2 minutes |
| Segment 2 | Temperature 60° C. | Time 2 minutes |
| Segment 3 | Temperature 70° C. | Time 0.5 minutes |
| Cycles = 45 | | |

4. Polarisation Measurements

These were taken on a Perkin Elmer LS-5B fluorimeter equipped with the manufacturer's polarisation accessory, providing polarising filters which can be set at 0° or 90°, positioned in the excitation and emission light paths. The wavelength settings used were:

|  | excitation (nm) | emission (nm) |
|---|---|---|
| for fluorescein: | 495 | 520 |
| for rhodamine: | 544 | 576 |

The fluorescence of the sample, ca. 2.0 ml, in a Hughes and Hughes disposable cuvette or 0.55 ml in a Perkin-Elmer 5200.4339 (examples 6 to 9), was measured with the filters set in four combinations:

|  | excitation filter | emmision filter |
|---|---|---|
| $(I_\perp)_V$ | vertical | horizontal |
| $(I_{11})_V$ | vertical | vertical |
| $(I_\perp)_H$ | horizontal | horizontal |
| $(I_{11})_H$ | horizontal | vertical |

The correction factor G was calculated from:

$$G = \frac{(I_{11})H}{(I_\perp)H}$$

and the polarisation value calculated:

$$P = \frac{(I_{11})_v - G(I_\perp)v}{(I_{11})_v + G(I_\perp)v}$$

All values quoted are the average of at least two replicates. All measurements were taken at ambient temperature, except where indicated otherwise.

5. Labelling of Oligonucleotides with Rhodamine

This was carried out using the fluoresceinylation procedure of section 2. (method B) but employing 1% rhodamine B isothiocyanate (Sigma) instead of fluorescein isothiocyanate.

6. Synthesis of a BSA Oligonucleotide 13 Conjugate:

6.1 Preparation of maleimido derivatised BSA

To a solution of BSA (Sigma, 10 mg/ml in 100 ul PBS/100 ul water) was added 0.1M triethanolamine HCl, 1 mM MgCl$_2$, 1 mmZnSO$_4$, pH 7.4 (0.6 ml), followed by 12 ul of a freshly prepared solution of SMCC (Pierce) in dry DMF (6.7 mg/ml) and the reaction mixture incubated at 25° C. for 30 min. The product was then purified by passage through a NAP 25 desalting column (Pharmacia) which had been primed with BSA (Boehringer molecular biology grade) and equilibrated in PBS. The product was collected in 1.6 ml and a portion taken for analysis. Protein concentration was assessed by OD at 280 nm (using an extinction coefficient of 0.62 for 1 mg/ml) whilst the maleimido concentration was assessed as follows: 0.15 ml of sample was reacted with 10 ul of 1mm mercaptoethanol for 30 min. at 37° C., alongside duplicate controls with 0.15 ml of buffer alone. The reactions were then diluted with 1.2 ml of PBS, zeroed at 412 nm in a spectrophotometer, and 25 µl of 1 mM 5,5,'dithiobis(2-nitro-benzoic acid) added. Remaining thiol concentrations were thereby measured using an extinction coefficient of 14150, the difference between sample and control enabled the maleimido concentration and hence the degree of substitution to be calculated. This value was found to be 1.7 moles maleimido per mole of protein.

6.2 Reaction of the 5' amino derivatised oligonucleotide with 2-iminothiolane and subsequent conjugation with BSA To an aqueous solution (0.2 ml) of the amino derivatised oligonucleotide (⅕th of a nominal 1 umole synthesis) was added a freshly prepared solution (0.3 ml) of 2-iminothiolane (5 mg/ml) in 0.2M sodium bicarbonate buffer pH 9.0 and the reaction incubated at 37° C. for 30 minutes. The product was then isolated by passage through a NAP 25 desalting column (Pharmacia) equilibrated in PBS, collecting the product in 1.6 ml. This was then immediately added to the BSA prepared as described above. The two components were then allowed to react overnight at 4° C.

The reaction was then concentrated to ca. 0.5 ml using a BSA blocked microconcentrator (Amicon) and applied to a column (ca. 45 ml) of Biogel P-100F (Biorad) equilibrated and run in 50 mM Tris buffer pH 7.5 at a flow rate of 0.14 ml/min. The eluted peaks were detected by UV absorbance at 260 nm and UV spectra of the fractions comprising the first peak, containing the conjugate were determined. Fractions containing absorbance contributions at both 260 and 280 nm were pooled. Later fractions containing increased 280 nm contributions, believed to be due to free BSA, were excluded.

EXAMPLE 1

Figure 1:
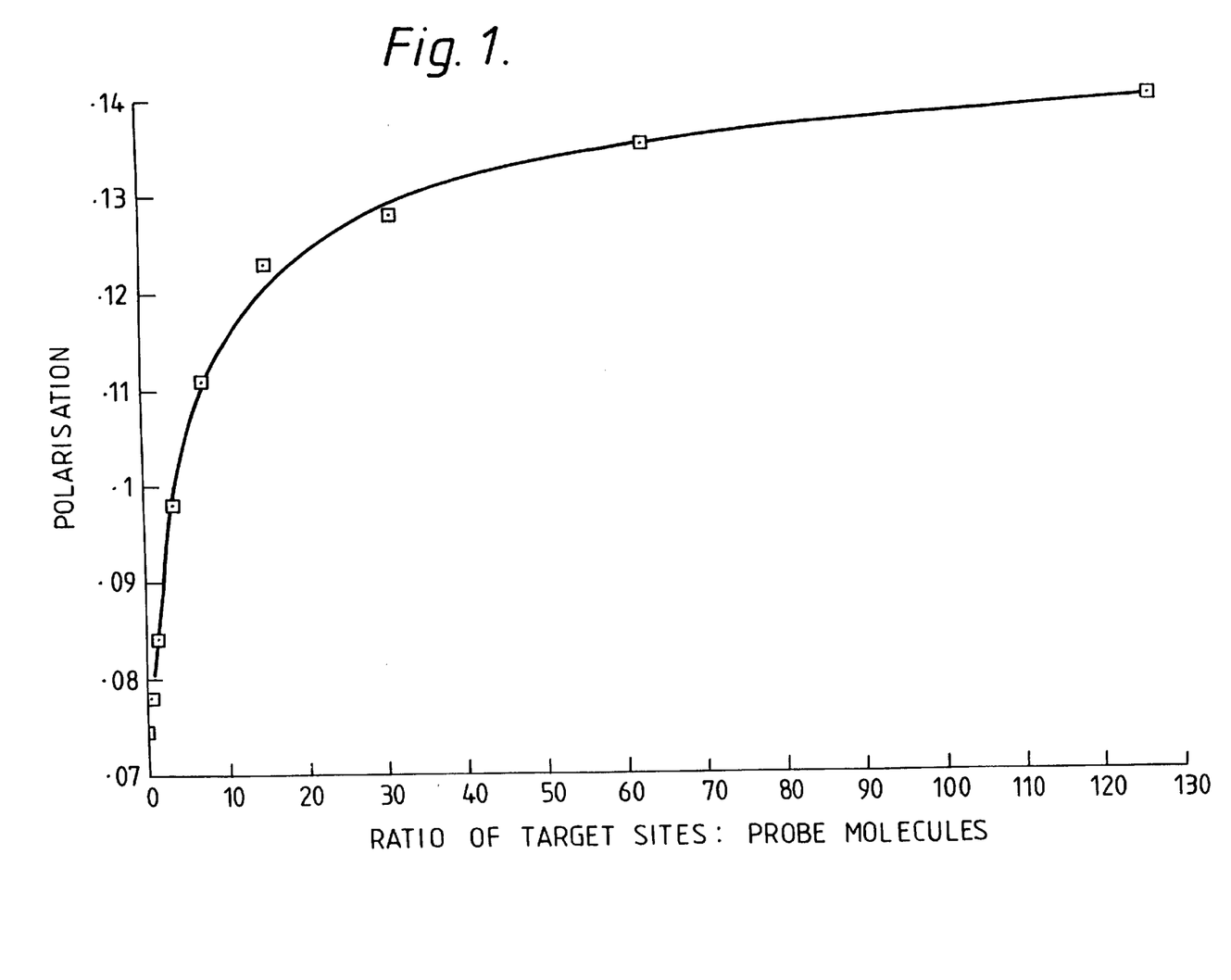
FIG. 1 shows a graph of the fluoresence polarisation of a 64 mer (T) and an 8 mer (P) against the ratio of target sites: probe molecules.

Hybridisation of a Fluoresceinylated 8-mer to a Synthetic 64-mer Oligonucleotide Target A 10$^{-7}$M solution (2.0 ml) of FL-oligo 1 was prepared in 10 mM Tris 1 mM EDTA pH 8.0 (2.0 ml) and 3M NaCl, 0.34M trisodium citrate (0.3 ml), and the polarisation value determined. To the cuvette was then added sequential aliquots of a 10$^{-4}$M, 10$^{-5}$M or 10$^{-6}$M solution of the 64-mer target, oligo 2, in 10 mM tris (hydroxymethyl) aminomethane, 1 mM EDTA pH 8.0, as shown in the table below, and the polarisation value determined after each addition. These data are tabulated below and illustrated in FIG. 1 and show that the presence of target produces an increase in polarisation value.

| Volume µl) added | | | Cumulative ratio of target 8-mer sites to probe | Polarisation |
|---|---|---|---|---|
| 10$^{-6}$M | 10$^{-5}$M | 10$^{-4}$M |  |  |
| — | — | — | — | 0.075 |
| 12.5 | — | — | 0.5 | 0.078 |
| 25 | — | — | 1.5 | 0.084 |
| — | 5.0 | — | 3.5 | 0.098 |
| — | 10.2 | — | 7.5 | 0.111 |
| — | 20.5 | — | 15.5 | 0.123 |
| — | — | 4.1 | 31.3 | 0.128 |
| — | — | 8.2 | 63.5 | 0.135 |
| — | — | 16.4 | 127.5 | 0.139 |

The specificity of the interaction was investigated using an unrelated oligonucleotide, oligo 3, as target. A 10$^{-7}$ M solution of Fl-oligo 1 was prepared in 10 mM tris (hydroxymethyl)aminomethane, 1 mM EDTA pH 8.0 (2.0 ml) and 3M NaCl, 0.3M trisodium citrate (0.1 ml) and the polarisation value determined. To the cuvette was then added oligo 2 to a concentration of 5×10$^{-7}$M and the polarisation value determined. This was then repeated using oligo 3 to the same concentration. The results obtained were

|               | Polarisation | SD(n = 4) |
|---|---|---|
| FL-oligo 1 alone | 0.0636 | 0.0015 |
| FL-oligo 1 + oligo 2 | 0.1091 | 0.0022 |
| FL-oligo 1 + oligo 3 | 0.0617 | 0.0019 |

The polarisation value obtained with the probe and the unrelated target was insignificantly different to that obtained with the probe alone, thus demonstrating specificity.

EXAMPLE 2

Detection of a PCR Product

The polymerase chain reaction was performed as described above using as the 5' primer, 100 pmoles of oligo 4 and as the 3' primer, 100 pmole of oligo 5.

The polarisation of fluorescence of 5.1 pmoles FL-oligo 6 in 2 ml 10 mM Tris HCl, 50 mM potassium chloride, 1.5 mM magnesium chloride, 0.01% gelatin (w/v) pH 8.3, was measured. The PCR product (100 μl) was boiled for 5 minutes and then cooled on ice for 5 minutes. This was added to the probe in the cuvette, mixed and, after 10 minutes, the polarisation of fluorescence was again measured.

| Results | Polarisation |
|---|---|
| Fluoresceinylated oligo 6 alone | 0.084 |
| Fluoresceinylated oligo 6 + PCR product | 0.155 |

The presence of the PCR product has caused a significant increase in the polarisation value.

EXAMPLE 3

Detection of a Single Stranded PCR Product

The polymerase chain reaction was performed as described. The 5' primer was 2 pmoles of oligo 7, the 3' primer was 100 pmoles of oligonucleotide 8. 40 cycles were employed.

The polarisation of fluorescence of 5.1 pmoles FL-oligo 6 in 2 ml 10 mM Tris HCl, 50 mM potassium chloride, 1.5 mM Magnesium chloride, 0.01% gelatin pH 8.3 was measured. The PCR product (100 μl) was added to the cuvette and mixed. The polarisation of fluorescence was measured after 10 minutes at room temperature.

| Results | Polarisation |
|---|---|
| Fluoresceinylated probe | 0.082 |
| Fluoresceinylated probe + PCR product | 0.148 |

The presence of PCR product has caused a significant increase in the polarisation value.

EXAMPLE 4

Detection of a Single Stranded PCR Product

The polymerase chain reaction was performed as described. The 5' primer was 2 pmole of oligo 4, the 3' primer was 100 pmoles of oligonucleotide 5.

The polarisation of fluorescence of 5.1 pmoles FL-oligo 6 in 2 ml 10 mM TrisHCl, 50 mM potassium chloride, 1.5 mM magnesium chloride, 0.01% gelatin pH 8.3 was measured. The PCR product (100 μl) was added to the cuvette and mixed. The polarisation of fluorescence was measured after 10 minutes at room temperature.

| Results | Polarisation |
|---|---|
| Fluoresceinylated probe | 0.084 |
| Fluoresceinylated probe + PCR product | 0.160 |

The presence of PCR product has caused a significant increase in the polarisation value.

EXAMPLE 5

Detection of an Extension Product

The polymerase chain reaction was performed as described previously but with the following programme:

| Segment 1 | Temperature 94° C. | Time 2 minutes |
|---|---|---|
| Segment 2 | Temperature 55° C. | Time 1.5 minutes |
| Segment 3 | Temperature 72° C. | Time 1 minute |

The 5' primer was 2 pmole of fluoresceinylated oligo nucleotide 6. The 3' primer was 100 pmole of oligonucleotide 5.

The polarisation of fluorescence of 5.1 pmoles of FL-oligo 6 in 2 ml 10 mM Tris HCl, 50 mM potassium chloride, 1.5 mM magnesium chloride, 0.01% gelatin pH 8.3, was measured.

The polarisation of fluorescence of 100 μl of PCR product in 2 ml 10 mM Tris HCl, 50 mM potassium chloride, 1.5 mM magnesium chloride, 0.01% gelatin pH 8.3 was similarly determined.

| Results | Polarisation |
|---|---|
| Fluoresceinylated primer | 0.080 |
| PCR product | 0.160 |

Incorporation of the primer into the PCR product has produced and increase in polarisation value.

EXAMPLE 6

Simultaneous Detection of Two Sequences Using Two Different Fluorophores.

Two separate synthetic targets A (oligo 9, a 97 mer) and B (oligo 10, a 90 mer) were detected both separately and together using a fluorescein labelled oligo F (FL-oligo 13), complementary to part of target A and a rhodamine labelled oligo R (RH-oligo 11), complementary to part of target B.

The polarisation of the probes F and R mixed (4 pmole of each) was measured in 0.45M NaCl, 0.05M trisodium citrate, 10 mM tris(hydroxymethyl)aminomethane pH 8.0 (0.55 ml) in the presence and absence of targets A and/or B.

|  | Polarisation (S.D.) | |
|---|---|---|
| Probe: | F | R |
| No target | 0.088 (0.003) | 0.243 (0.004) |
| Target A | 0.184 (0.006) | 0.253 (0.009) |
| Target B | 0.087 (0.005) | 0.311 (0.002) |
| Target A and B | 0.193 (0.005) | 0.316 (0.009) |

It can be seen that in the presence of target A, the corresponding probe F shows an increase in polarisation, and likewise the polarisation of R is increased in the presence of target B. Both probes show increased polarisation values when the two targets are present together. This demonstrates that the presence or absence of two different DNA sequences can be independently measured in the same cuvette.

EXAMPLE 7
Detection of a PCR Product Using Three Fluorescein Labelled Oligonucleotides Human DNA (25 ng) was amplified by PCR (45 cycles) using as primers oligo 7 (1 pmole) and oligo 8 (100 pmole). 3 tubes were combined and the DNA was treated with phenol (Sevag solution, 100 ul), vortexed and centrifuged for 2 minutes at 13,000 rpm. After removing the phenol layer, the solution was extracted 3 times with ether. 3M sodium acetate was added (38.5 ul), followed by ethanol (1 ml). After cooling at −70° C. for 15 minutes the tubes were spun as above and the pellets redissolved in 3×SSC, 50 mM tris(hydroxymethyl)aminomethane, pH 8.0 (500 ul).

Fluoresceinylated oligos 12, 13 and 14 (3 pmole of each) were added to 3×SSC, 50 mM Tris, pH 8.0 (0.550 ml) and the fluorescence polarisation determined, both separately and as a mixture. The measurement was then repeated in the presence of the above PCR product (500 ul), after incubation at 50° C. for 30 minutes and cooling to room temperature.

|  | polarisation (SD, n = 5) | fluorescence v/v* |
| --- | --- | --- |
| FL-oligo 12 alone | 0.096 (0.004) | 716 |
| FL-oligo 13 alone | 0.103 (0.008) | 524 |
| FL-oligo 14 alone | 0.091 (0.009) | 553 |
| FL-oligos 12, 13 and 14 | 0.073 (0.010) | 1772 |
| FL-oligos 12, 13 and 14 + related PCR product | 0.137 (0.004) | 1600 |

*both polarising filters vertically aligned (units are arbitary)

It can be seen that the mixture of the three probes gives a high polarisation in the presence of target. The higher fluorescence readings obtained with probe mixtures allows either better precision and robustness in the readings and/or allows lower probe concentrations to be used with concommitant improvements in sensitivity. cl EXAMPLE 8
Enhancement of Polarisation Increase upon Hybridisation Using a Bovine Serum Albumin (BSA) Conjugated Probe Fluorescein labelled oligo 14 (3 pmole) was added to 3×SSC, 50 mM Tris, pH 8.0 (0.5 ml) in the prescence and absence of 8 pmole of synthetic target oligo 9, and the polarisation value determined. To this was then added BSA oligo 13 conjugate (27 pmole) and, after a 10 minute incubation at room temperature, the polarisation was again measured.

|  | Polarisation (SD) (n = 5) |
| --- | --- |
| FL-oligo 14 alone | 0.091 (0.009) |
| FL-oligo 14 + target | 0.164 (0.004) |
| FL-oligo 14 + BSA/oligo 13 | 0.094 (0.007) |
| FL-oligo 14 + target + BSA/oligo 13 | 0.189 (0.004) |

It can be seen that the presence of the complementary BSA oligo conjugate has significantly enhanced the increase in polarisation brought about by the hybridisation of the fluorophore labelled probe to the target.

EXAMPLE 9
Assay for an Oligonucleotide Target by Competition with a Homologous Probe for a Complementary DNA Strand The BSA conjugated oligonucleotide 13 (7 pmole) was mixed with varying concentrations of synthetic target oligo 9 in 0.45M NaCl, 0.05M trisodium citrate, 10 mM Tris pH 8.0 (0.55 ml) and to this was added the fluorescently labelled oligo 15 (3 pmole), complementary to the BSA oligo conjugate.

| amount of target (pmole) | fluorescence polarisation | S.D. (n = 3) |
| --- | --- | --- |
| 0 | 0.121 | 0.005 |
| 1 | 0.116 | 0.002 |
| 2 | 0.098 | 0.004 |
| 3 | 0.096 | 0.008 |
| 6 | 0.092 | 0.003 |
| probe 1533 alone | 0.084 | 0.008 |

It can be seen that the increasing concentrations of target bring about a progressive decrease in fluorescence polarisation and that this assay may therefore be used to estimate the concentration of target DNA in the sample.

EXAMPLE 10
Detection of a PCR Product with a Fluorescent Probe: Effect of Temperature Three cuvettes containing a) 1×SSC (2 ml), b) 1×SSC (2 ml) containing FL-oligo 6 (5.1 pmole) and c) 1×SSC (2 ml) containing FL-oglio 6 (5.1 pmole) and the complementary asymmetric PCR product (ca. 7 pmole) generated by primers under the standard PCR conditions using oligo 7 (2 pmole) and oligo 5 (100 pmole) as primers, were placed in the thermostated cell holder of the fluorimeter. A thermocouple device was placed in cuvette a).

The fluorescence polarisation of cuvettes b) and c) was determined at ambient temperature (22° C.) and the temperature of the water circulating through the cell holder increased in steps to give a range of sample temperatures. At each point, the temperature was heald steady for 5 minutes and the polarisation then determined.

Results

Figure 2:
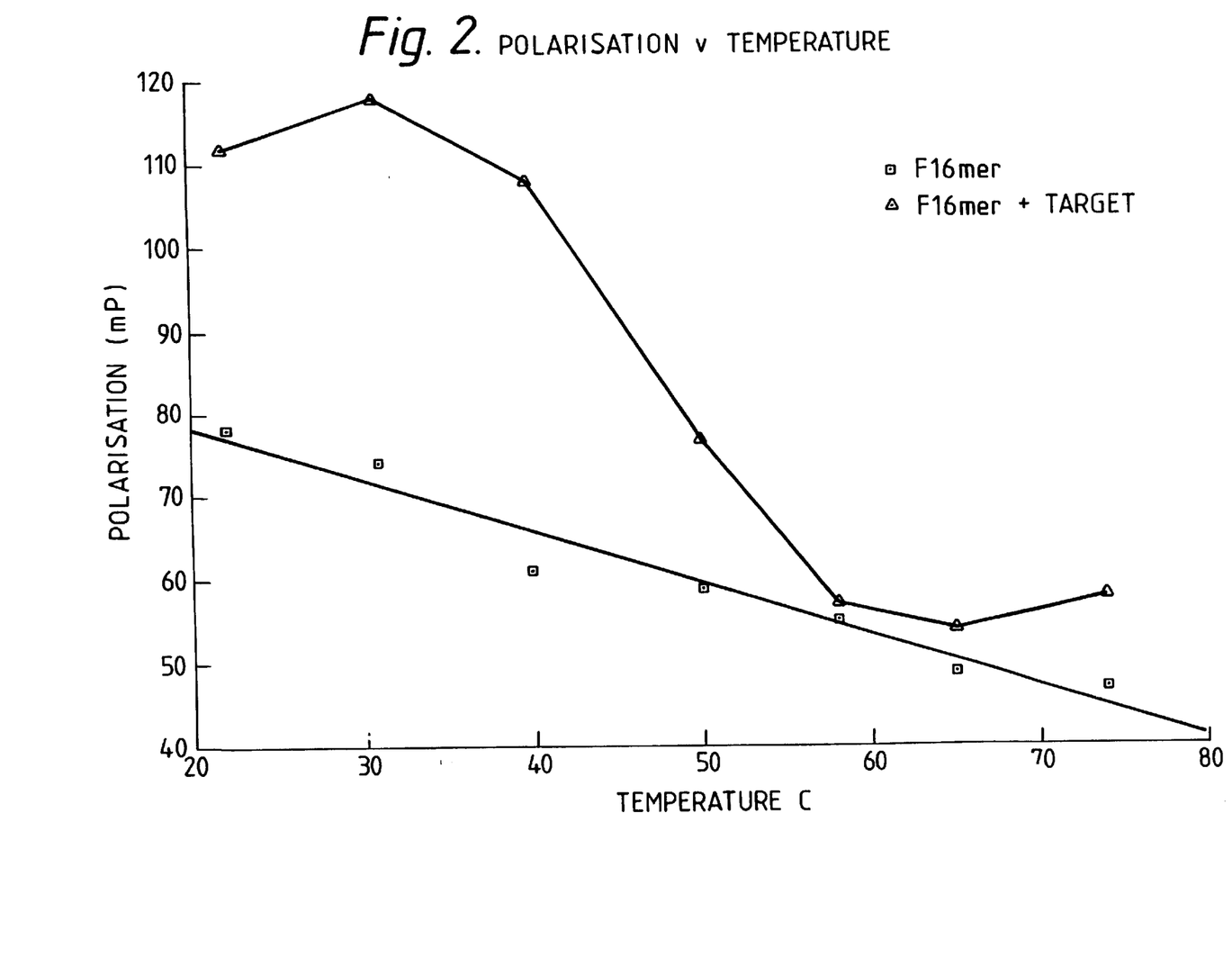
FIG. 2 shows the effect of temperature on the assay of a PCR product using a fluorescent probe. The PCR product was generated using oligonucleotides 4 and 5 as primers.

The results are plotted in FIG. 2. For the probe alone there is the general expected decrease in polarisation due to the increased tumbling as the temperature increases. The higher polarisation of the hybrid is sustained until ca. 50° C. when, presumably due to the melting of the hybrid, the polarisation reverts to that of the free probe.

EXAMPLE 11
Detection of a PCR Product Using a Fluorescent Probe: Effect of Salt Concentration Three cuvettes were set up containing in water (2 ml): a) 5.1 pmole of FL-oligo 6, b) 5.1 pmole of FL-oligo 6 and ca. 6 pmole of the complementary PCR product used in example 10 and c) 5.1 pmole of FL-oligo 6 and a large excess (1.4 nmole) of an unrelated 50-mer oligonucleotide. The salt concentration was increased by addition of aliquots of 20×SSC to give a range of concentrations up to 5×SSC final concentration, and the fluorescence polarisation measured after each addition.

Results

Figure 3:
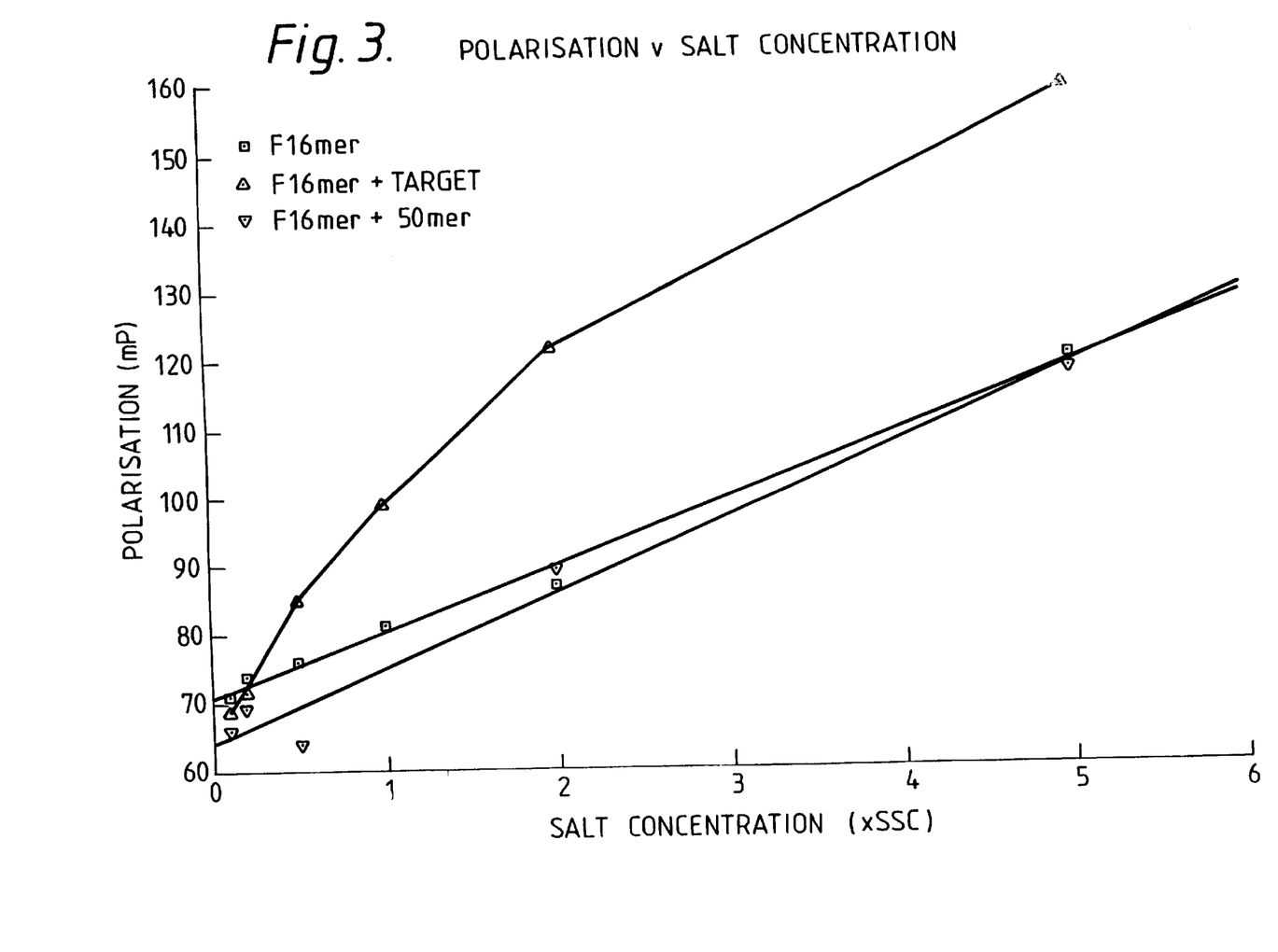
FIG. 3 shows the effect of salt concentration on the assay of a PCR product using oligonucleotides 4 and 5 as primers, and an unrelated sequence, using a fluorescent probe.

The results are shown in FIG. 3. There is an overall increase in polarisation with salt concentration due, at least in part, to the increased viscosity of the solvent. Above 0.5×SSC, a clear enhancement of the polarisation due to the probe binding to the target DNA is apparent, this enhancement not occuring in the cuvette containing the large excess of non-target.

We claim:

1. An assay method for detecting the presence, absence or quantity of a target nucleic acid sequence in a sample also containing other nucleic acids which are not sought to be detected which method comprises contacting the sample nucleic acid with a fluorescent polynucleotide probe capable of hybridisation with the target nucleic acid sequence in homogenous solution and detecting the presence or absence of such hybridisation by fluorescence polarisation wherein the presence of said hybridisation is detected by a change in polarisation of the fluorescent polynucleotide probe in the presence of said sample and in the absence of said sample.

2. A method as claimed in claim 1 which comprises the use of two or more fluorescently labelled probes which hybridise to different regions of the target nucleic acid sequence.

3. A method as claimed in claim 1 wherein when the target nucleic acid is derived from a double-stranded nucleic acid and the strand complementary to the target nucleic acid is present in the sample one or more blocking polynucleotides are hybridised to a region adjacent to the target nucleic acid sequence to prevent annealing of the complementary strand and target nucleic acid sequence.

4. A method for the detection of a target nucleic acid sequence in a sample, which method comprises contacting the sample with (i) a complementary polynucleotide capable of hybridisation to the target polynucleotide sequence and (ii) a fluorescent polynucleotide probe capable of hybridisation to the same region as the target on the complementary polynucleotide, in homogeneous solution and detecting by fluorescence polarisation the presence or absence of hybridisation of the fluorescent polynucleotide probe with the complementary polynucleotide.

5. A method as claimed in claim 1 wherein the target nucleic acid sequence is a product of sample nucleic acid amplification and is essentially single stranded DNA.

6. A method as claimed in claim 4 wherein the target nucleic acid sequence is a product of sample nucleic acid amplification and is essentially single stranded DNA.

7. A method as claimed in claim 1 wherein the hybridised species to be detected by fluorescence polarisation includes one or more macromolecule-polynucleotide conjugate which is hybridised to the target nucleic acid sequence, wherein the conjugate comprises a macromolecule and single stranded nucleic acid.

8. A method as claimed in claim 4 wherein one or more macromolecules are attached to the complementary polynucleotide by covalent bonding or by a specific binding partner, one such partner being attached to the macromolecule and the other being attached to the complementary polynucleotide.

9. A method as claimed in claim 5 or 6 wherein a specific binding partner is incorporated into the target nucleic acid sequence before or during amplification and contacted with a complementary specific binding partner-macromolecule conjugate after amplification.

10. A method for the detection of a target nucleic acid sequence in a sample which comprises contacting sample nucleic acid with a fluorescent polynucleotide primer capable of hybridisation with the target sequence, subjecting any hybrid formed to primer extension and detecting the presence or absence of primer extended product by fluorescence polarisation.

11. A method as claimed in claim 10 which comprises a polymerase chain reaction and wherein a first fluorescent polynucleotide primer is employed at a lower concentration than a second polynucleotide primer such that a measurable quantity of amplification product is obtained.

12. A method as claimed in claim 10 wherein two polynucleotide primers are employed each priming opposite strands of the sample nucleic acid and both primers are incorporated into the amplified product and wherein one primer is labelled with a fluorophore and a macromolecule is attached to the other primer, which macromolecule is a protein or water-soluble polymer.

13. A method as claimed in claim 10 wherein two polynucleotide primers are employed each priming opposite strands of the sample nucleic acid and both primers are incorporated into the amplified product and wherein one primer is labelled with a fluorophore and a macromolecule is attached to the other primer and wherein the macromolecule is non-covalently attached via specific binding partner to the primer after amplification.

14. A method as claimed in claim 10 wherein two polynucleotide primers are employed each priming opposite strands of the sample nucleic acid and both primers are incorporated into the amplified product and wherein one primer is labelled with a fluorophore and a macromolecule is attached to the other primer and wherein the macromolecule is non-covalently attached via specific binding partners to the primer after amplification and wherein the specific binding partners are (i) biotin and (ii) avidin or streptavidin.

15. A method as claimed in claim 1 wherein the sample is a biological sample.

16. A method as claimed in claim 4 wherein the sample is a biological sample.

17. A method as claimed in claim 10 wherein the sample is a biological sample.

18. An assay method for assessing the presence or absence or quantity of a target nucleic acid sequence in a sample, which target nucleic acid is of biological origin or an amplification product thereof, which method comprises contacting the sample nucleic acid with a fluorescent polynucleotide probe capable of hybridization with the target nucleic acid sequence in homogenous solution and detecting the presence or absence of such hybridization by fluorescence polarisation.

19. The assay method according to claim 18 wherein the presence or absence of said target nucleic and sequence is assessed.

20. The assay method according to claim 1 or claim 18 wherein the fluorescent polynucleotide probe contains a fluorophore which does not intercalate with nucleic acids.

21. The assay method according to claim 1 or claim 18 wherein the presence or absence of said hybridization is detected solely by fluorescence polarisation.

* * * * *